(12) United States Patent
Kwak et al.

(10) Patent No.: US 8,830,486 B2
(45) Date of Patent: Sep. 9, 2014

(54) ATMOSPHERIC MOLECULAR CONTAMINATION CONTROL WITH LOCAL PURGING

(75) Inventors: Hidong Kwak, San Jose, CA (US);
Ward Dixon, Livermore, CA (US);
Torsten Kaack, Los Altos, CA (US);
Ning-Yi Neil Wang, Fremont, CA (US);
Jagjit Sandhu, Fremont, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 72 days.

(21) Appl. No.: 13/536,410

(22) Filed: Jun. 28, 2012

(65) Prior Publication Data

US 2013/0010311 A1   Jan. 10, 2013

Related U.S. Application Data

(60) Provisional application No. 61/504,271, filed on Jul. 4, 2011.

(51) Int. Cl.
| | |
|---|---|
| *G01B 11/28* | (2006.01) |
| *G01N 21/55* | (2014.01) |
| *G01B 11/06* | (2006.01) |
| *B08B 5/02* | (2006.01) |
| *H01L 21/67* | (2006.01) |
| *H01L 21/66* | (2006.01) |

(52) U.S. Cl.
CPC ............ *B08B 5/02* (2013.01); *G01B 11/0641* (2013.01); *H01L 22/12* (2013.01); *G01B 2210/56* (2013.01); *H01L 21/67017* (2013.01)
USPC .......................................... 356/630; 356/445

(58) Field of Classification Search
CPC ....................................................... G01N 21/03
USPC .................... 356/244–246, 630, 237.1–237.5
See application file for complete search history.

(56) References Cited

U.S. PATENT DOCUMENTS

| | | |
|---|---|---|
| 2008/0154410 A1 | 6/2008 | Nakamura |
| 2008/0180698 A1 | 7/2008 | Kwak et al. |
| 2008/0252889 A1 | 10/2008 | Fielden et al. |
| 2010/0099268 A1* | 4/2010 | Timans ........................ 438/761 |
| 2011/0216318 A1* | 9/2011 | Nagaike ....................... 356/337 |

FOREIGN PATENT DOCUMENTS

JP     56069503     6/1981

* cited by examiner

*Primary Examiner* — Michael P Stafira
(74) *Attorney, Agent, or Firm* — Suiter Swantz pc llo

(57) ABSTRACT

A local purging tool for purging a portion of a surface of a wafer with purging gas is disclosed. The purging tool includes a purging chamber configured to contain purging gas within a cavity of the purging chamber, a permeable portion of a surface of the purging chamber configured to diffuse purging gas from the cavity of the chamber to a portion of a surface of a wafer, and an aperture configured to transmit illumination received from an illumination source to a measurement location of the portion of the surface of the wafer and further configured to transmit illumination reflected from the measurement location to a detector.

7 Claims, 10 Drawing Sheets

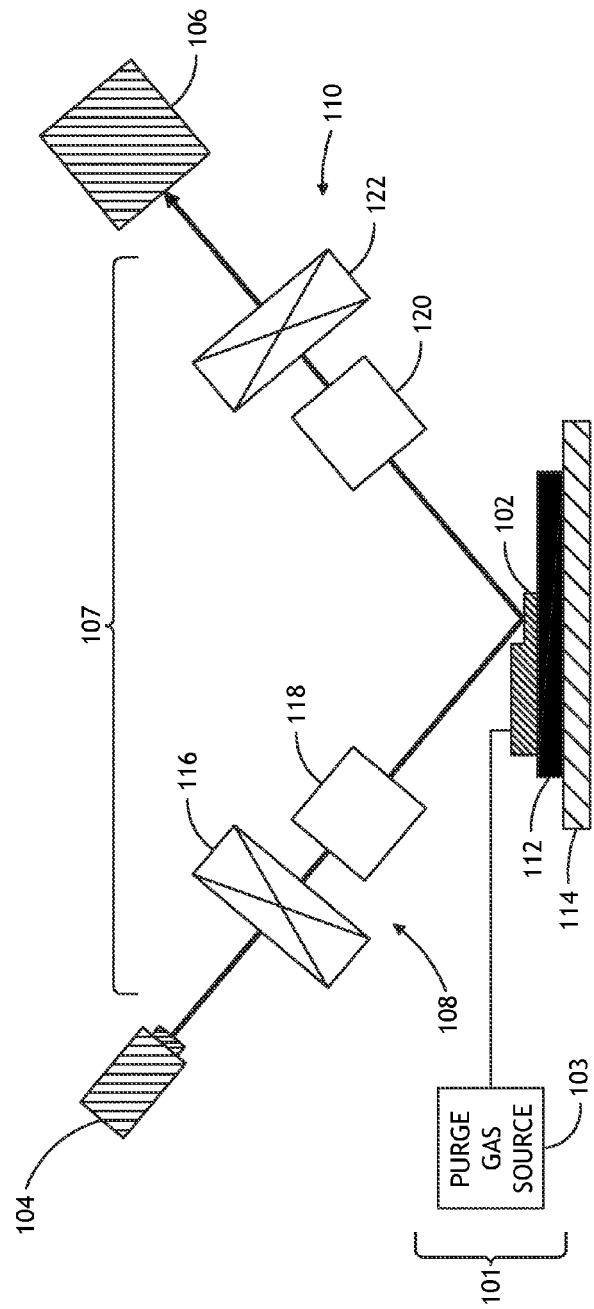

ATMOSPHERIC MOLECULAR CONTAMINATION CONTROL WITH LOCAL PURGING

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

For purposes of the USPTO extra-statutory requirements, the present application constitutes a regular (non-provisional) patent application of United States Provisional Patent Application entitled ATMOSPHERIC MOLECULAR CONTAMINATION (AMC) CONTROL WITH NITROGEN LOCAL PURGING AFTER AMC CLEAN, naming Hidong Kwak, Ward Dixon, Torsten Kaack, Ning Yi Neil Wang, and Jagjit Sandhu, as inventors, filed Jul. 4, 2011, Application Ser. No. 61/504,271.

TECHNICAL FIELD

The present invention relates to the field of optical metrology, and in particular to system and method for locally purging a portion of a surface of a wafer to improve measurement accuracy.

BACKGROUND

Industrial applications continue to require semiconductor devices with more demanding specifications. To meet the increasing demand, most modern semiconductor fabrication processes include thin film metrology systems and other optical systems to obtain characteristic information about thin films formed on a given semiconductor wafer, such as a silicon wafer. For example, thin films may include oxide, nitride, and/or metal layers, among others. Characteristics such as the thickness and composition of each thin film must be tightly controlled during the manufacturing process to ensure proper performance of the resulting semiconductors. Accordingly, optical systems are used at various steps throughout the semiconductor manufacturing process.

The accuracy of most modern optical systems is limited, however, by atmospheric molecular contamination "AMC" that may accumulate on the surface of a thin film and distort the film thickness or other physical characteristic measured or analyzed by an ellipsometer or other optical system. Atmospheric molecular contaminants can be removed from the surface of a thin film with a variety of techniques such as the use of energy beams or heating to a sufficiently high temperature. However, AMC continues to accumulate in the interim period between AMC removal and taking characteristic measurements. Therefore, it is necessary to inhibit re-accumulation of AMC on a thin film surface after it is cleaned in order to make accurate characteristic measurements and observations. Accordingly, the present invention overcomes the foregoing problems by providing an efficacious and relatively inexpensive solution for controlling AMC accumulation.

SUMMARY

A system and method for local purging of a portion of a surface of a wafer with purging gas is disclosed. In one aspect, the system may include a local purging tool for purging a portion of a surface of a wafer with purging gas, the local purging tool including a purging chamber configured to contain purging gas within a cavity of the purging chamber; a permeable portion of a surface of the purging chamber configured to diffuse purging gas from the cavity of the chamber to a portion of a surface of a wafer; and an aperture configured to transmit illumination received from an illumination source to a measurement location of the portion of the surface of the wafer and further configured to transmit illumination reflected from the measurement location to a detector.

In another aspect, the system may include a system for performing optical metrology on a locally purged wafer, the system including an illumination source; a detector configured to receive illumination reflected from a measurement location of a portion of a surface of a wafer; a local purging system comprising a local purging tool configured to purge the portion of the surface of the wafer, the local purging tool including a purging chamber configured to contain purging gas within a cavity of the purging chamber; a permeable portion of a surface of the purging chamber configured to diffuse a portion of purging gas from the cavity of the chamber to the portion of the surface of the wafer; and an aperture configured to transmit illumination received from the illumination source to the measurement location of the portion of the surface of the wafer and further configured to transmit illumination reflected from the measurement location to the detector. The system may further include a purge gas source fluidically connected to the local purging tool.

In another aspect, a method for determining a thickness correction for a thickness measurement of a thin film on a surface of a wafer, includes the steps of establishing a correlation between relative humidity and measured thickness of a thin film on a surface of a wafer; acquiring an initial humidity level measurement of an environment proximate to a measurement location of a portion of the surface of the wafer; acquiring a thickness measurement of the thin film from the measurement location, wherein the portion of the surface of the wafer is locally purged when the thickness measurement is acquired; acquiring a subsequent humidity level measurement of the environment proximate to the measurement location, wherein the subsequent measurement is associated with the thickness measurement of the thin film; calculating a differential between the initial humidity level measurement and the subsequent humidity level measurement; and determining a thickness correction for the thickness measurement of the thin film utilizing the established correlation between relative humidity and measured thickness and the calculated differential between the initial humidity level measurement and the subsequent humidity level measurement.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which:

FIG. 1A is a block diagram of a system for performing optical metrology on a locally purged wafer.

DETAILED DESCRIPTION OF THE INVENTION

Figure 1B:
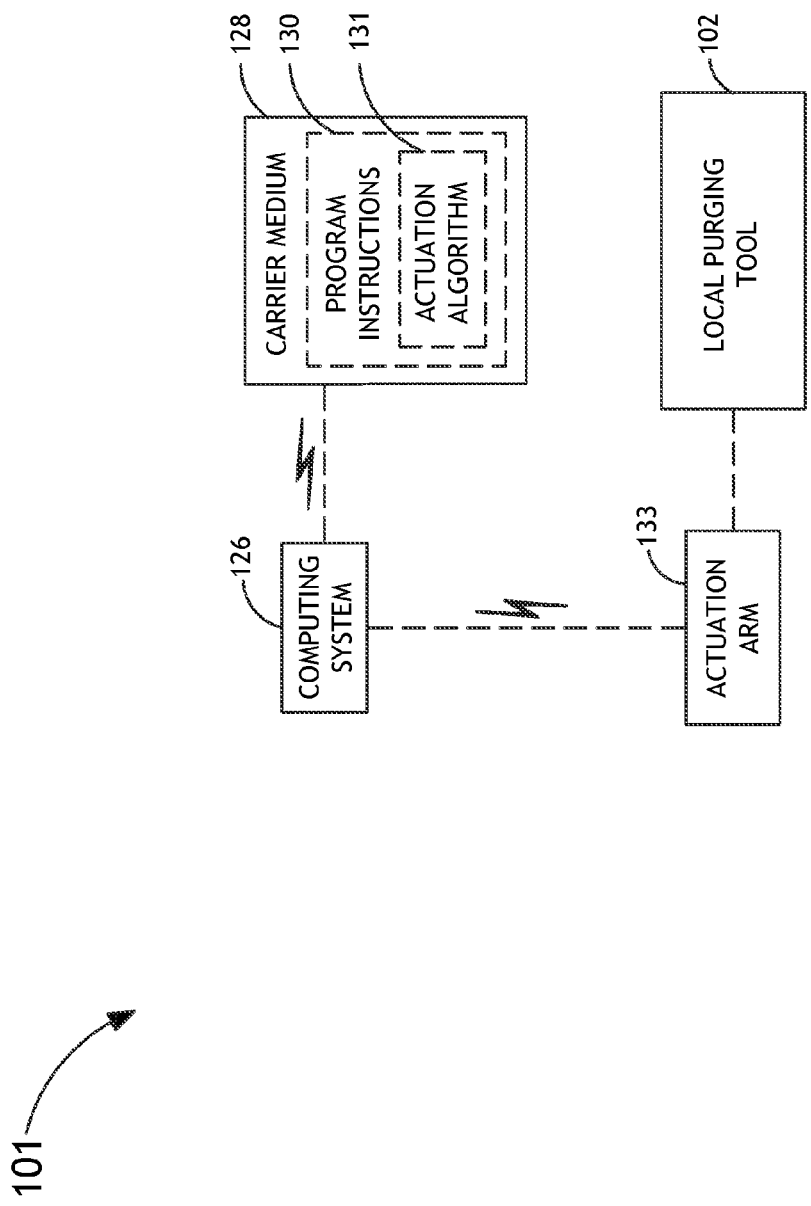
FIG. 1B is a block diagram of a system for actuating a local purging tool.

Reference will now be made in detail to the subject matter disclosed, which is illustrated in the accompanying drawings.

Referring generally to FIGS. 1A through 3, a system and method for locally purging a portion of a surface of a wafer is described in accordance with the present disclosure. Optical systems are commonly utilized to measure or analyze physical characteristics of thin films formed on a substrate such as a silicon wafer commonly employed in the manufacture of semiconductors. Atmospheric molecular contamination ("AMC"), such as hydrocarbons and other contaminants, tends to accumulate on surfaces of wafers and impair optical systems from obtaining proper information related to the physical characteristics of one or more wafers being measured or analyzed by the optical system. The present invention is directed to a system and method for preventing accumulation of AMC on the surface of a wafer by local purging of at least a portion of the surface of the wafer with a purging gas such as, but not limited to, nitrogen, argon, neon gas and the like.

As used throughout the present disclosure, the term "wafer" generally refers to a substrate formed of a semiconductor or non-semiconductor material. For example, semiconductor or non-semiconductor materials include, but are not limited to, monocrystalline silicon, gallium arsenide, and indium phosphide. A wafer may include one or more layers. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

As used throughout the present disclosure, the term "thin film" generally refers to one or more layers formed on a wafer. For example, such layers may include, but are not limited to, a resist, a dielectric material, a conductive material, and a semiconductive material. Many different types of such layers are known in the art, and the term thin film as used herein is intended to encompass all types of such layers which may be formed on a wafer.

As used throughout the present disclosure, the term "optical system" generally refers to any system utilizing illumination to detect one or more physical characteristics of a thin film or a wafer such as thickness, composition, size, shape, structure, configuration, conductivity, reflectivity, or any other physical measurement. For example, such optical systems may include, but are not limited to, a spectroscopic ellipsometer, a single-wavelength ellipsometer, a spectroscopic reflectometer, a single wavelength reflectometer, or any other metrology system. While the present invention is discussed in the context of metrology systems, it is further contemplated that some or all of the presently disclosed elements could be extended to an inspection system or any other system utilizing optical technology to make measurements.

FIG. 1A illustrates a system 100 for performing metrology on a locally purged portion of a surface of a wafer 112. In one embodiment the system 100 may include an optical system 107 for providing metrology for a portion of the surface of the wafer 112. The system 100 may further include a local purging system 101 configured to locally purge the portion of the surface of the wafer 112 with purging gas to inhibit accumulation of AMC on the portion of the surface of the wafer 112. The portion of the surface of the wafer 112 may include a measurement location to which the optical system 107 transmits illumination (e.g. visible light, vacuum ultraviolet, ultraviolet, infrared, etc.) to provide metrology for one or more of the wafer's 112 physical characteristics.

Referring to FIG. 1B, the local purging system 101 may include a local purging tool 102 configured to diffuse purging gas to the portion of the surface of the wafer 112. The local purging tool 102 may be configured to purge the portion of the surface of the wafer 112 by manual or computer aided placement of the local purging tool 102 proximate to the portion of the surface of the wafer 112. In an embodiment utilizing computer aided placement, a computing system 126 may be communicatively coupled to an actuation arm 133 mechanically coupled to the local purging tool 102. The computing system 126 may be configured to provide the actuation arm 133 with instructions for properly placing the local purging tool 102 in a desired position and orientation. In some embodiments, the desired position may be a position proximate to the portion of the surface of the wafer 112 selected by a user. In other embodiments, the desired position may be a position determined by the computing system 126 based on the measurement location. The actuation arm 133 may include one or more motors, servos, step motors, hydraulics, robotics, or any other devices or components for rotating or translating the local purging tool 102. The computing system 126 may include at least one carrier medium 128 such as a flash, solid-state, optical, random access or other static or dynamic memory device configured with program instructions 130 including an actuation algorithm 131. Actuation algorithms are known to the art, such as algorithms for controlling motors, servos, or other devices that can be actuated via electrical signals for robotically rotating or translating a mechanically coupled apparatus such as the local purging tool 102.

Figure 1C:
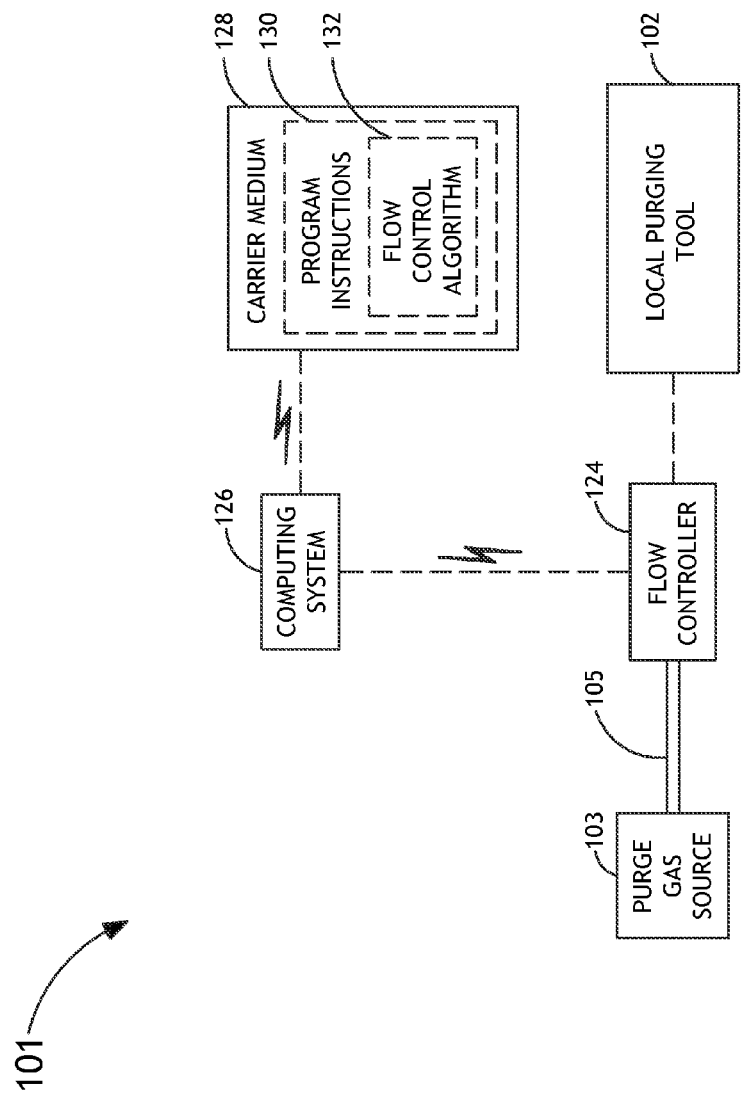
FIG. 1C is a block diagram of a system for controlling flow of purging gas from a purge gas source to a local purging tool.

Referring to FIG. 1C, the local purging system 101 may include a purge gas source 103 fluidically connected to the local purging tool. The purge gas source 103 may be configured to supply the local purging tool 102 with purging gas. The purge gas source 103 may be any suitable container for containing a purging gas such as a pressurized tank or any other pressurized container.

In a further embodiment, the local purging system 101 may include a flow controller 124 fluidically connected in between the purge gas source 103 and the local purging tool 102. The flow controller 124 may be configured to control the rate at which purging gas is supplied to the local purging tool 102. The flow controller 124 may include one or more valves, regulators, pumps, or any other means for regulating the pressure or rate at which purging gas moves through at least one conduit 105 fluidically connecting the flow controller 124 to the local purging tool 102.

In a further embodiment, the flow controller 124 may be communicatively connected to the computing system 126 configured to provide the flow controller 124 with instructions for setting the rate at which purging gas flows to the local purging tool 102. The computing system 126 may include at least one carrier medium 128 such as a flash, solid-state, optical, random access or other static or dynamic memory device configured with program instructions 130 including a flow control algorithm 132. Flow control algorithms 132 are known to the art, such as algorithms for configuring a pressure valve that may be included in the flow controller 124. For example, the flow control algorithm 132 may direct the flow controller 124 to actuate the pressure valve based on a correlation between the pressure valve's mechanical properties and a desired flow rate. In some embodiments, a user selected rate of 10 to 100 LPM (liters per minute) may be the desired flow rate for locally purging the portion of the surface of the wafer 112 with a purging gas. Other flow rates outside the 10-100 LPM range may be desirable depending on the properties of particular purging gases and the composition of the underlying thin film or wafer 112. The foregoing flow rate range is included by way of example only and is not intended to limit the system in any way.

Figure 1D:
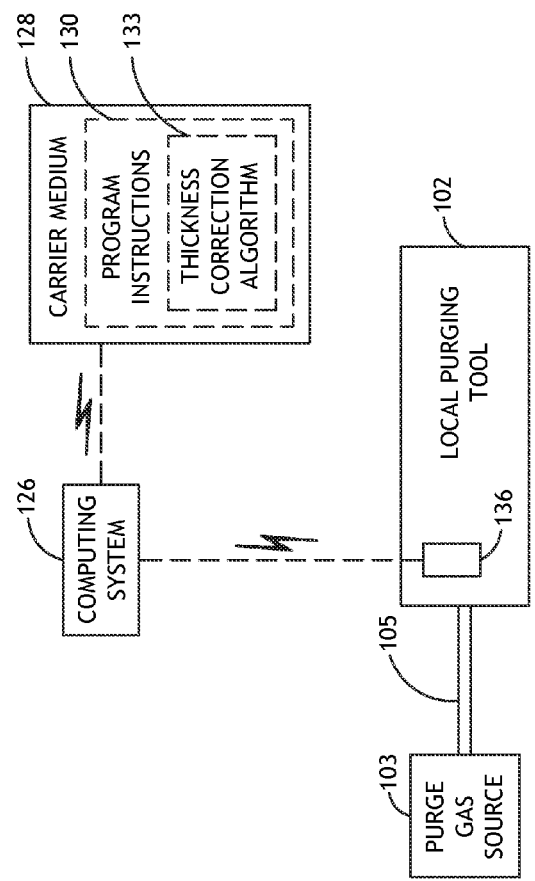
FIG. 1D is a block diagram of a system for determining a thickness correction.

Referring to FIG. 1D, the local purging system may include a humidity sensor 136 configured for measuring the humidity level of an environment proximate to the measurement location. The environment may be a locally purged environment proximate to the portion of the surface of the wafer 112. The humidity sensor 136 may be communicatively coupled to the computing system 126 and further configured to transmit a humidity level measurement to the computing system 126. The computing system 126 may be configured to receive humidity level measurement from the humidity sensor 136 and further configured to determine a thickness correction for a thickness measurement of a thin film of the wafer 112. The thickness correction may be an error level, deviation, distortion, or adjustment to the measured thickness of the thin film based on a change in the humidity level of the environment proximate to the measurement location and a correlation between the relative humidity level and measured thickness of the thin film. In one embodiment, correlation between the relative humidity level and measured thickness of the thin film may include a known value programmed on a carrier medium. In another embodiment the correlation may be determined by a calibration algorithm or the correlation may be a user selected value. The computing system 126 may include at least one carrier medium 128 such as a flash, solid-state, optical, random access or other static or dynamic memory device configured with program instructions 130 including a thickness correction algorithm 134.

In one embodiment, the thickness correction algorithm 134 may require the computing system 126 complete one or more of the following steps: (i) establish a correlation between the relative humidity level and measured thickness of the thin film; (ii) acquire an initial humidity level measurement of the environment proximate to the measurement location; (iii) acquire a thickness measurement of the thin film of the wafer 112 from the detector 106 of the optical system; (iv) acquire a subsequent humidity level measurement of the environment, wherein the subsequent humidity level measurement associated with the measured thickness of the thin film, (v) calculate the differential between the initial humidity level measurement and the subsequent humidity level measurement, and (vi) determine the thickness correction utilizing the correlation between the relative humidity level and measured thickness of the thin film and the calculated differential between the initial humidity level measurement and the subsequent humidity level measurement. A method 300 of determining a thickness correction for the measured thickness of the thin film, alluded to by the foregoing discussion of the thickness correction algorithm 134, will be described in further detail.

In some embodiments the humidity sensor 136, while previously discussed in the context of a local purging system 101 with a local purging tool 102, is not limited to such a system. The humidity sensor 136 may alternatively be placed within any atmospherically controlled environment proximate to the measurement location of the surface of the wafer 112.

Figure 2A:
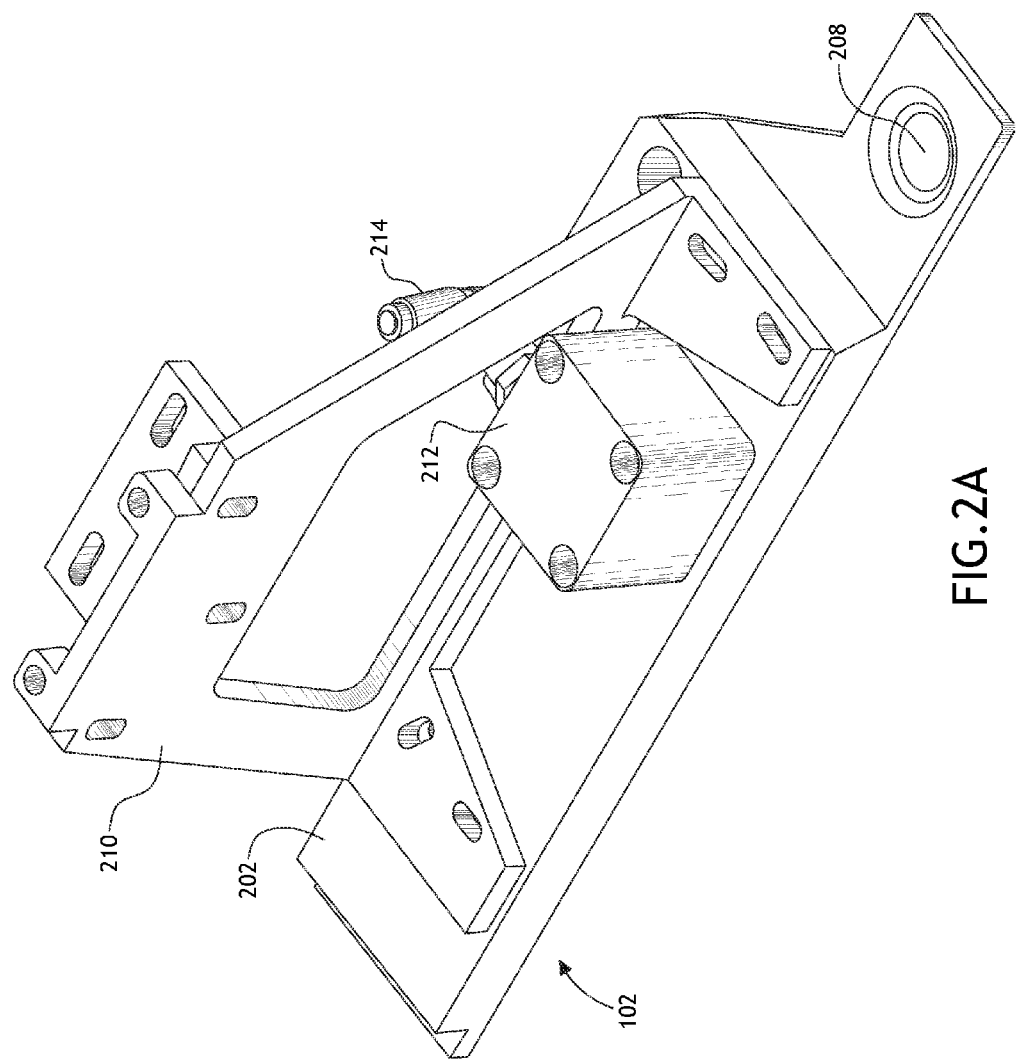
FIG. 2A illustrates a conceptual view of a local purging tool.
Figure 2B:
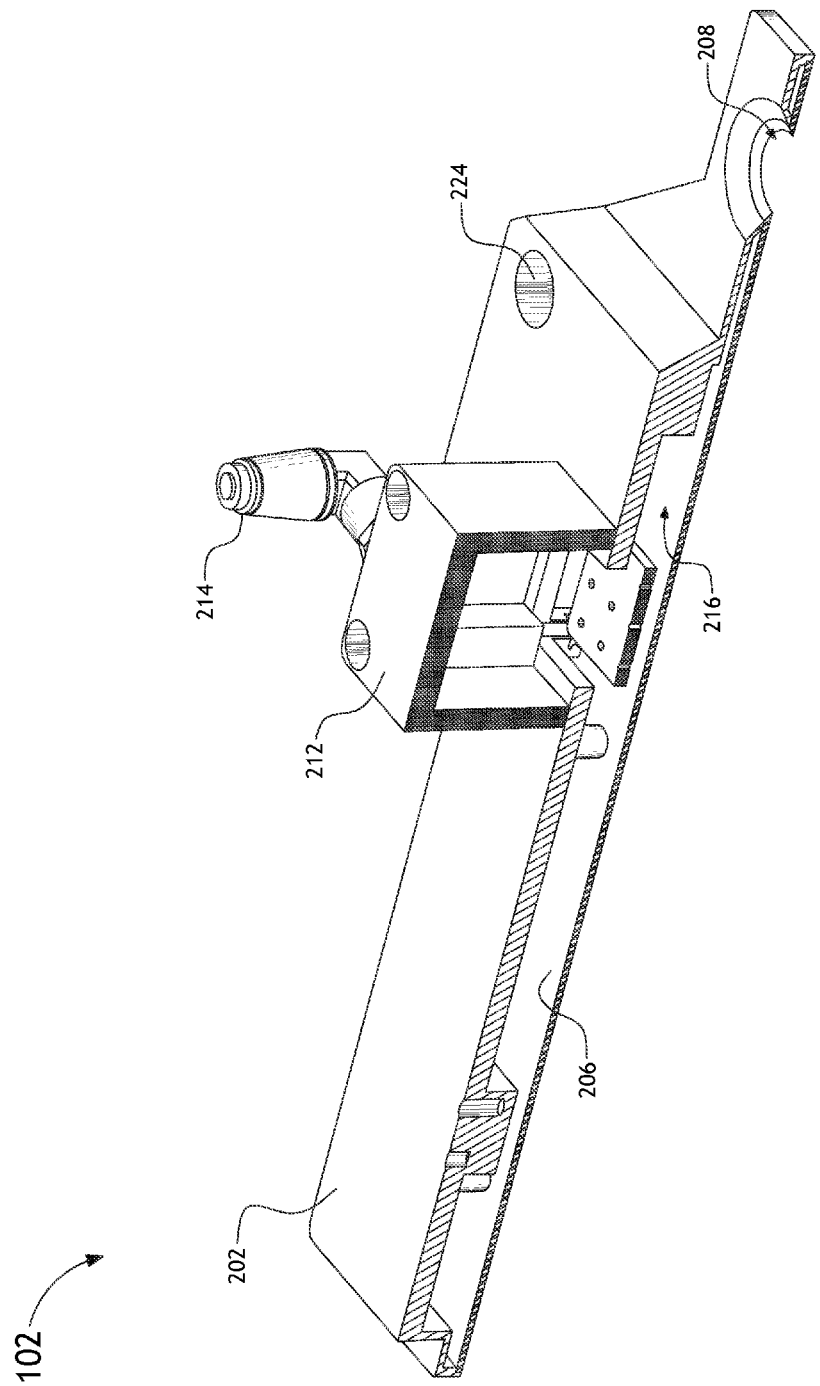
FIG. 2B illustrates a conceptual view of a longitudinal cross-section of a local purging tool.

FIGS. 2A through 2E illustrate many aspects and various embodiments of the local purging tool 102. Referring to FIGS. 2A and 2B, the local purging tool 102 may include a purging chamber 202 configured to contain purging gas within a purging cavity 216 making up an interior portion of the purging chamber 202. The local purging tool 102 may further include a gas intake port 214 configured to receive purging gas from the purge gas source 103 and further configured to transmit a portion of the received purging gas to the purging cavity 216 of the purging chamber 202. The local purging tool 102 may further include a gas intake chamber 212 in between the gas intake port 214 and the purging chamber 202.

Figure 2C:
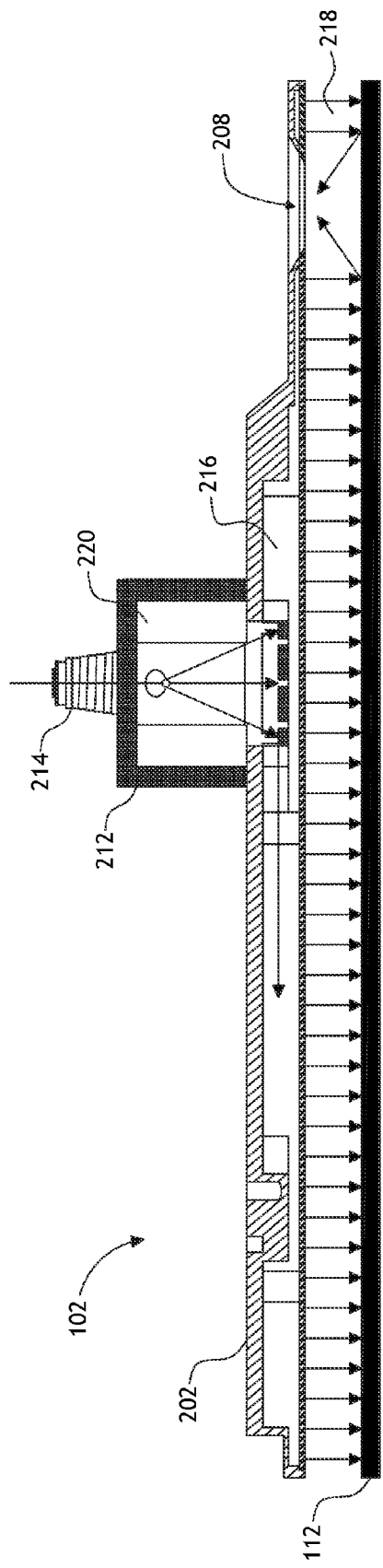
FIG. 2C illustrates a conceptual view of purging gas flow from a longitudinal cross-section of a local purging tool.
Figure 2D:
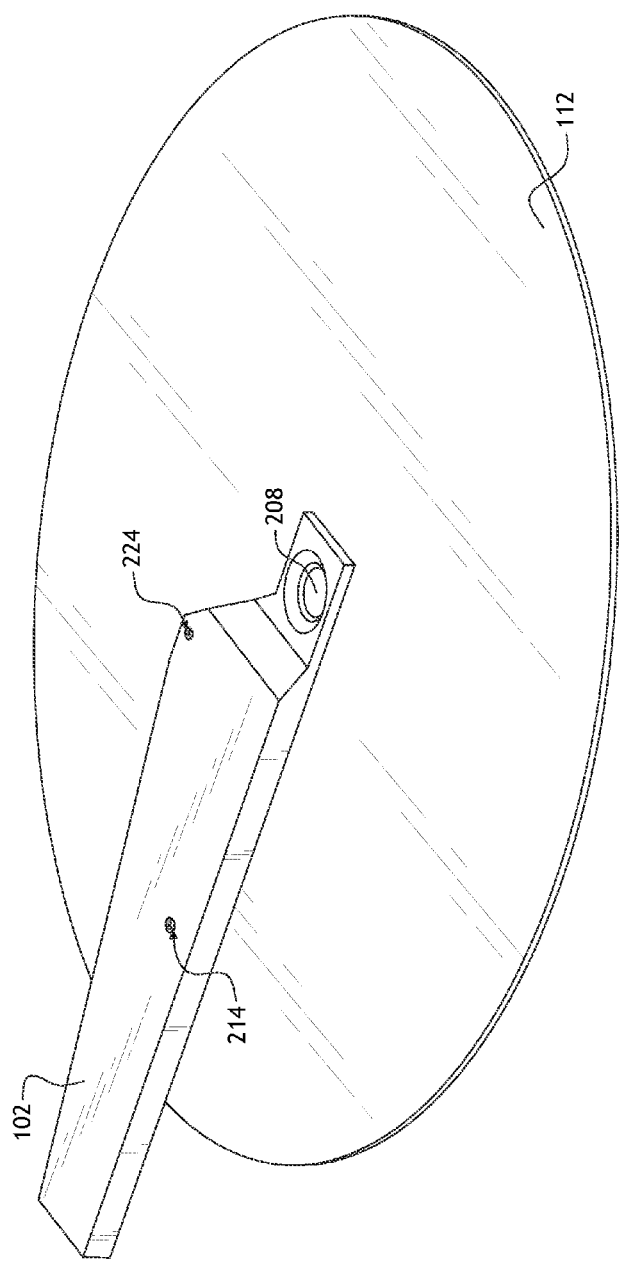
FIG. 2D illustrates a conceptual view of a local purging tool positioned proximate to a portion of a surface of a wafer.

Referring to FIG. 2C, the gas intake chamber 212 may be configured to contain a portion of purging gas received from a purge gas source 103 through the gas intake port 214 within a gas intake cavity 220 making up an interior portion of the gas intake chamber 212. The gas intake chamber 212 may be further configured to distribute a portion of the purging gas throughout a substantial portion of the purging cavity 216 of the purging chamber 202. The gas intake chamber 212 may allow purging gas received through the gas intake port 214 to be distributed in a substantially even manner throughout the purging cavity 216. For example, the gas intake chamber 212 may include structural elements to disperse purging gas flowing from the gas intake port 214 through the gas intake chamber 212 to the purging chamber 202. In some embodiments, the purging chamber 202 may include one or more of the elements of the gas intake chamber 212.

Figure 2E:
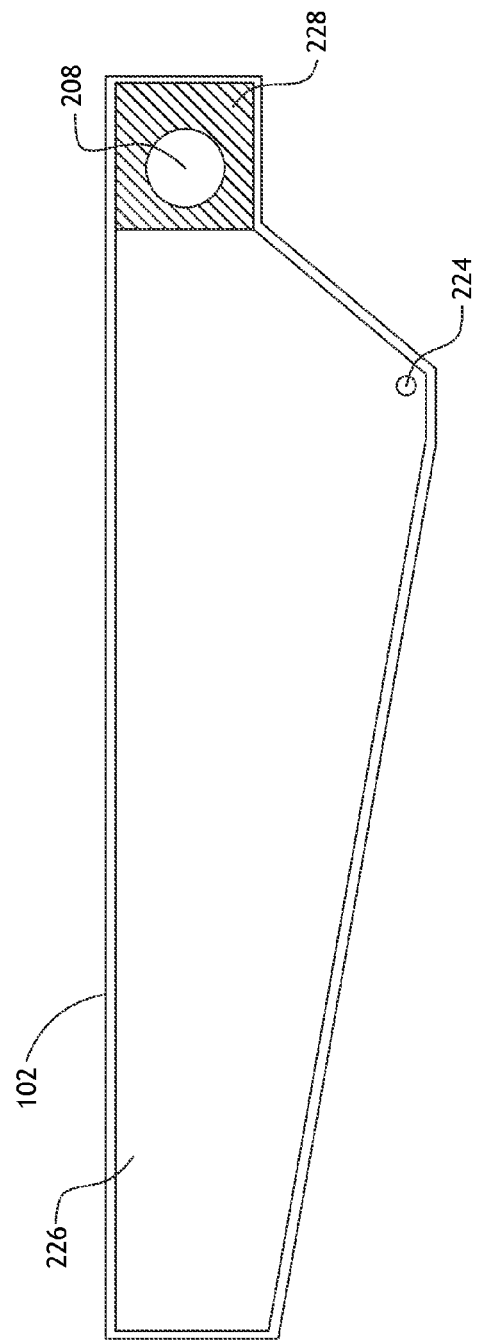
FIG. 2E illustrates a conceptual view of a permeable portion of a surface of purging chamber of a local purging tool.

As shown in FIG. 2B, the local purging tool 102 may include a permeable portion 206 of a surface of the purging chamber 202. The permeable portion 206 may be configured to diffuse purging gas from the within the purging cavity 216 to locally purge the portion of the surface of the wafer 112. The permeable portion 206 may include a porous material penetrable by purging gas. Referring to FIG. 2E, the permeable portion 206 may further include a first portion 226 and a second portion 228. The first portion 226 may be a different grade of permeable media than the second portion 228 such that the first portion 226 may be configured to diffuse purging gas at a different rate that the second portion 228. For example, in some embodiments it may be desirable to diffuse purging gas at a higher rate near the measurement location than the rate at which purging gas is diffused to a remainder of the portion of the surface of the wafer 112.

As shown in FIG. 2A, the local purging tool 102 may further include an aperture 208 configured to receive illumination from the optical system 107. The aperture 208 may be further configured to transmit illumination to a detector of the optical system 107. The local purging tool 102 may be positioned such that the aperture 208 may be located proximate to the measurement location of the portion of the surface of the wafer 112. The aperture 208 may be configured to transmit illumination received from the optical system 107 to the measurement location. The aperture 208 may be further configured to transmit illumination reflected from the measurement location to a detector 106 (via a collection arm) of the optical system 107. Accordingly, the aperture may be configured to allow the optical system 107 to utilize illumination to measure or analyze physical characteristics of the wafer 112 at the measurement location proximate to the local purging tool 102.

In one embodiment, the aperture 208 may be located within the permeable portion 206 of the surface of the purging chamber 202. In this regard, the aperture may allow for local purging of the measurement location by purging gas diffused through the permeable portion 206, while also being configured to receive illumination from an illumination source of the optical system 107. In particular, FIG. 2C depicts the purging gas flow 218 in one embodiment of the local purging tool 102. Purging gas diffused from the permeable portion 206 may flow to the portion of the surface of the wafer 112 such that the portion of the surface of the wafer 112 including the measurement location may be purged. Purging gas may also deflect from the portion of the surface of the wafer 112 to flow through the aperture 208 in a direction away from the portion of the surface of the wafer 112 such that AMC cannot enter the aperture 208 to contaminate the locally purged portion of the surface of the wafer 112.

In another embodiment, the aperture 208 may be located in the second portion 228 of the permeable portion 206 of the surface of the purging chamber 202. The second portion 228 may be configured to diffuse purging gas at a different rate that the first portion 226 such that the rate purging gas is diffused around the aperture is different from the rate at which purging gas is diffused to the remainder of the portion of the surface of the wafer 112. For example, the second portion 228 may include higher grade porous material than the first portion 226, such that purging gas is diffused at a higher rate around the aperture 208. In addition, the aperture 208 may be located proximate to the measurement location such that purging gas is diffused at a higher rate proximate to the measurement location than the rate at which purging gas is diffused across the remainder of the locally purged portion of the surface of the wafer 112.

As shown in FIG. 2A, the local purging tool 102 may further include a beam port 224 configured to engage an energy beam source or to receive an energy beam for displacing AMC from the portion of the surface of the wafer 112. Energy beam sources and energy beams for displacing AMC from the surfaces of wafers are known to the art, such as those used in KLA-TENCOR Corporation's iDESORBER technology. The beam port 224 may be further configured to transmit at least a portion of the energy beam to the portion of the surface of the wafer 112 to clean AMC from the portion of the surface prior to or concurrent with local purging of the portion of the surface of the wafer 112.

In an additional aspect, the local purging tool 102 may be configured to be mechanically coupled to the actuation arm (not shown) to enable at least one of translational and rotational movement of the local purging tool 102 to a desired position or orientation proximate to the surface of the wafer 112 so that the portion of the surface of the wafer 112 may be purged. Referring to FIG. 2A, the local purging tool 102 may include a bracket 210 configured to mechanically engage the actuation arm so that the actuation arm may actuate the local purging tool 102 to a desired position. In some embodiments, the desired position may be a user selected position or a position determined in accordance with the measurement location.

Referring again to FIG. 1A, an embodiment of the system 100 will be discussed in further detail. The system 100 may be configured to receive a wafer 112. The wafer 112 may include one or more thin films. The wafer 112 may be configured to receive illumination at the measurement location on the portion of the surface of the wafer 112. The wafer 112 may be further configured to reflect illumination from the measurement location. The system may further include a sample stage 114 configured to hold the wafer 112 in the course of metrology. The sample stage 114 may be further configured to actuate the wafer 112 to a desired position or orientation. The sample stage 114 may be further configured to actuate the wafer 112 to a position that enables the wafer 112 to receive illumination at the measurement location.

The system 100 may further include an optical system 107 configured to provide metrology in order to measure one or more physical characteristics of the wafer 112. The optical system 107 may include an illumination arm 108 configured for providing illumination to a portion of the surface of the wafer 112. The illumination arm 108 may include an illumination source 104 for providing illumination to the portion of the surface of the wafer 112. The illumination source 104 may include one or more illumination sources known in the art, commonly identified by one or more wavelengths within the electromagnetic spectrum (e.g. vacuum ultraviolet, ultraviolet, visible, infrared, etc.). The illumination arm 108 may further include a polarizer 116 to polarize illumination received from the illumination source 104. The polarizer 116 may contain one or more polarizing elements known to the art such as a linear polarizer, among others. The illumination arm 108 may further include one or more illumination optical elements 118 (e.g. retarder, quarter wave plate, focus optics, phase modulators, etc.) to modulate illumination received from the illumination source 104. The illumination arm 108 may be further configured to transmit illumination from the illumination source 104 to the measurement location of the portion of the surface of the wafer 112. The measurement location may reflect at least a portion of the illumination received from the illumination arm 108.

The optical system 107 may include a collection arm 110 configured to receive illumination reflected from the measurement location of the portion of the surface of the wafer 112. The collection arm 110 may include a detector 106 configured to receive illumination reflected from the measurement location. The detector 106 may be any suitable detector known to the art, such as a spectrometer, for analyzing or measuring characteristics of illumination (e.g. amplitude, phase, polarity, frequency, etc.). The collection arm 110 may further include an analyzer 122 to polarize illumination reflected from the measurement location. The analyzer 122 may contain one or more polarizing elements known to the art such as a linear polarizer, among others. The collection arm 110 may further include one or more collection optical elements 120 (e.g. retarder, quarter wave plate, focus optics, phase modulators, etc.) to modulate illumination reflected from the measurement location.

The system 100 may further include the local purging system 101 configured for locally purging the portion of the surface of the wafer 112 with purging gas. The purge gas source 103 of the local purging system 101 may be configured to supply purging gas to the local purging tool 102 to diffuse purging gas across the portion of the surface of the wafer 112 to inhibit accumulation of AMC on the portion of the surface of the wafer 112. The aperture 208 of the local purging tool 102 may be configured to receive illumination from the illumination arm 108 of the optical system 107. The aperture 208 may be further configured to transmit illumination received from the illumination arm 108 to the measurement location of the portion of the surface of the wafer 112. The aperture 208 may be further configured to transmit illumination reflected from the measurement location to the collection arm 110 of the optical system 107. In this regards, the optical system 107 may be configured to measure one or more of the physical characteristics of the wafer 112 at the measurement location of the portion of the surface of the wafer 112 while the portion of the surface of the wafer 112 is locally purged.

In one embodiment, the system 100 may be configured for measuring the thickness of the thin film of the wafer 112. The illumination arm 108 of the optical system 107 may transmit illumination to the measurement location through the aperture 208 of the local purging tool 102. Illumination reflected from the measurement location may be transmitted through the aperture 208 of the local purging tool 102 to the collection arm 110 of the optical system 107. The collection arm 110 may be further configured to transmit information relating to the illumination received by the detector 106 to the computing system 126. The computing system 126 may be further configured to determine the thickness of the thin film utilizing an algorithm know in the art, such as those algorithms commonly used for ellipsometry.

In a further embodiment, the system 100 may be configured for correcting the thickness measurement of the thin film of the wafer 112 with the method 300 hereafter described. The thickness measurement of the thin film may be distorted by atmospheric variables such as AMC accumulation on the surface of the wafer 112. A thickness correction to adjust the thickness measurement to a corrected thickness value may be determined by utilizing the correlation between the relative humidity level and measured thickness of the thin film. Referring to FIG. 1D, the system 100 may include one or more humidity sensor 136 configured to detect the humidity level of the environment proximate to the portion of the surface of the wafer 112. In one embodiment, the humidity sensor 136 may be located within the cavity 216 of the purging chamber 202 of the local purging tool 102. In another embodiment, the humidity sensor 136 may be located on an external surface of the local purging tool 102. The foregoing examples are only intended to illustrate possible locations for the humidity sensor 136 but should not be construed in a manner to limit the placement of the humidity sensor 136 with respect to the environment proximate to the portion of the surface of the wafer 112. The humidity sensor 136 may be communicatively coupled to the computing system 126 configured to execute the thickness correction algorithm 134 from program instructions 130 on the carrier medium 128.

Figure 3:
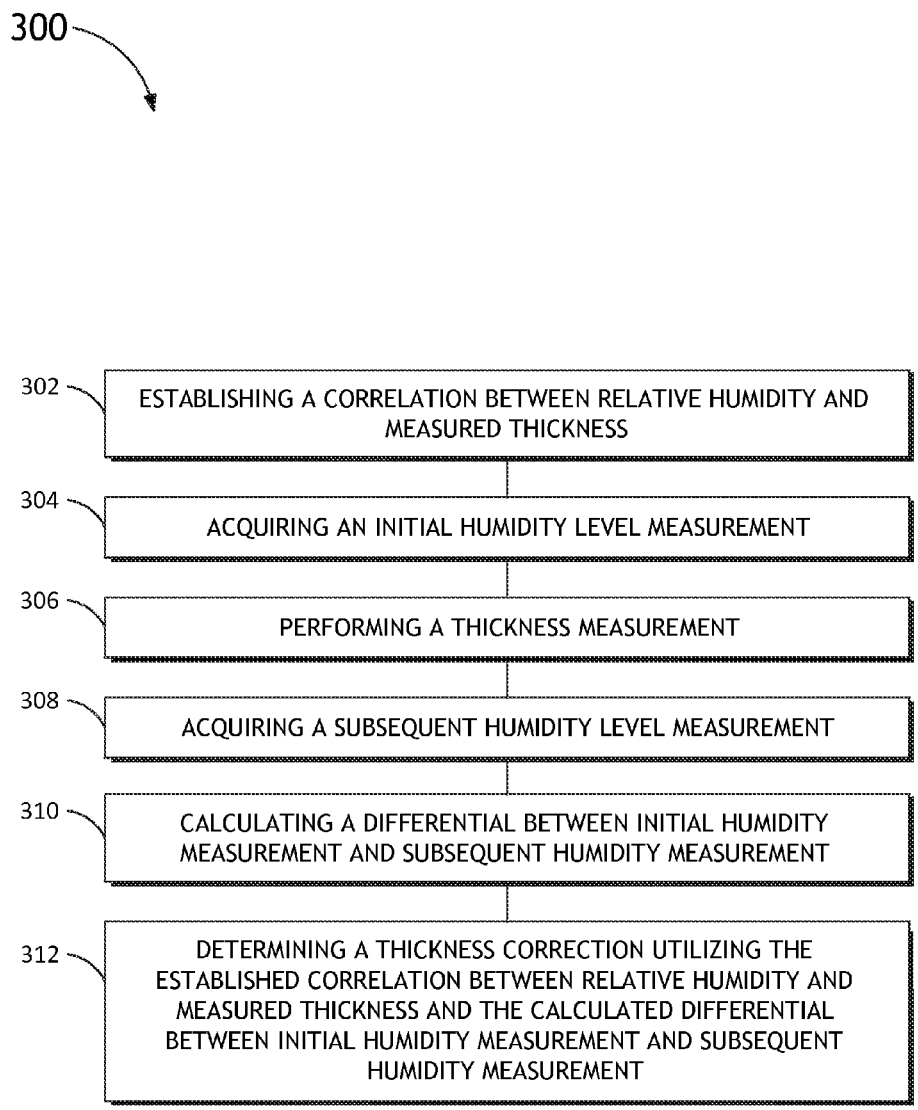
FIG. 3 is a flow diagram of a method for determining a thickness correction.

Referring to FIG. 3, a method 300 for determining a thickness correction for a thickness measurement is illustrated in accordance with one embodiment of the present invention. The method 300 may include: (i) step 302, establishing a correlation between the relative humidity level and measured thickness of the thin film; (ii) step 304, acquiring an initial humidity level measurement of the environment proximate to the measurement location; (iii) step 306, making a thickness measurement of the thin film of the wafer 112 at the measurement location of the portion of the surface of the wafer 112 with the optical system 107; (iv) step 308, acquiring a subsequent humidity level measurement of the environment, wherein the subsequent humidity level measurement is related to the measured thickness of the thin film; (v) step 310, calculating the differential between the initial humidity level measurement and the subsequent humidity level measurement; and (vi) step 312, determining the thickness correction utilizing the correlation between the relative humidity level and measured thickness of the thin film and the calculated differential between the initial humidity level measurement and the subsequent humidity level measurement.

In step 302, the correlation between the relative humidity level and measured thickness of the thin film may be established by utilizing a known value or approximation. For example, the correlation may be a standard or accepted value programmed on the carrier medium 128 of the computing system 126, or the correlation value may be a user selected value. Alternatively, the correlation value between the relative humidity level and measured thickness of the thin film may be established by a calibration method including one or more of the following steps: (i) acquiring an initial thickness measurement of the thin film; (ii) acquiring an initial humidity level measurement that is associated with the initial thickness measurement; (iii) acquiring a subsequent thickness measurement of the thin film; (iv) acquiring a subsequent humidity level measurement that is associated with the subsequent thickness measurement; (v) calculating a differential between the initial and subsequent thickness measurements; (vi) calculating a differential between the initial and subsequent humidity level measurements; and (vii) determining a correlation between relative humidity and measured thickness utilizing the calculated differential for the initial and subsequent thickness measurements and the calculated differential for the initial and subsequent humidity level measurements.

In step 304, the initial humidity level may be communicated from the humidity sensor 136 to the computing system 126. In one embodiment, the humidity sensor 136 may be configured to make the initial humidity level measurement substantially simultaneous to or immediately after the time at which AMC is displaced or removed from the portion of the surface of the wafer 112. The AMC may be removed with an energy beam or by heating the wafer 112 or the portion of the surface of the wafer 112 to a sufficiently high temperature.

In step 306, the detector 106 of the optical system 107 of the system 100 may be configured to make one or more thickness measurements of the thin film of the wafer 112 by receiving illumination reflected from the measurement location of the portion of the surface of the wafer 112. The detector 106 may be further configured to communicate data regarding the illumination reflected from the measurement location to the computing system 126. The computing system 126 may be further configured to calculate the thickness measurement of the thin film of the wafer 112 utilizing data received from the detector 106 regarding the illumination reflected from the measurement location.

In step 308, the humidity sensor 136 may make one or more subsequent humidity level measurements, at least one of which corresponds or relates to the humidity level at the time the thickness measurement was made by the optical system 107. The humidity sensor 136 may communicate the subsequent humidity level corresponding or relating to the thickness measurement to the computing system 126.

In step 310, the computing system 126 may be configured to calculate the differential between the initial humidity level and the subsequent humidity level that corresponds to the thickness measurement made by the optical system 107. The computing system 126 may be configured to calculate the differential by finding the mathematical difference between the initial humidity level measurement and the subsequent humidity level measurement. Alternatively, the computing system 126 may be configured to calculate the differential utilizing advanced mathematical techniques (e.g. polynomial approximations, differential equations, numerical transformations, etc.)

In step 312, the computing system 126 may be further configured to determine a thickness correction, such as an error level, deviation, distortion, adjustment, or other corrective variable utilizing a mathematical relationship between the differential between the initial and subsequent humidity level measurements and the correlation between the relative humidity level and measured thickness of the thin film. The computing system 126 may be further configured to apply the thickness correction to the thickness measurement of the thin film to determine the corrected thickness value for the thin film of the wafer 112.

It should be recognized that the various steps described throughout the present disclosure may be carried out by a single computing system 126 or, alternatively, a multiple computing system 126. Moreover, different subsystems of the system 100, such as the optical system 107 or the local purging system 101, may include a computing system suitable for carrying out at least a portion of the steps described above. Therefore, the above description should not be interpreted as a limitation on the present invention but merely an illustration. Further, the one or more computing systems 126 may be configured to perform any other step(s) of any of the method embodiments described herein.

The computing system 126 may include, but is not limited to, a personal computing system, mainframe computing system, workstation, image computer, parallel processor, or any other device known in the art. In general, the term "computing system" may be broadly defined to encompass any device having one or more processors, which execute instructions from a memory medium.

Program instructions 130 implementing methods such as those described herein may be transmitted over or stored on carrier medium 128. The carrier medium may be a transmission medium such as a wire, cable, or wireless transmission link. The carrier medium 128 may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. A local purging tool for purging a portion of a surface of a wafer with purging gas, comprising:
    a purging chamber configured to contain purging gas within a cavity of the purging chamber, the purging chamber being positionable relative to the surface of the wafer to a local purging portion of the wafer, the wafer being external to the cavity of the purging chamber;
    a permeable portion of a surface of the purging chamber configured to diffuse purging gas from the cavity of the purging chamber to the local purging portion of the surface of the wafer; and
    an aperture configured to transmit illumination received from an illumination source to a measurement location of the local purging portion of the surface of the wafer and further configured to transmit illumination reflected from the measurement location to a detector.

2. The local purging tool of claim 1, wherein the local purging tool further comprises a gas intake port configured to receive purging gas from a purge gas source and further configured to transmit purging gas to the cavity of the purging chamber.

3. The local purging tool of claim 1, wherein the local purging tool further comprises a beam port configured to transmit an energy beam emanating from an energy beam source to the local purging portion of the surface of the wafer to displace atmospheric molecular contamination from the local purging portion of the surface of the wafer.

4. The local purging tool of claim 1, wherein the local purging tool is mechanically coupled to an actuation arm configured to actuate the local purging tool to a position proximate to the local purging portion of the surface of the wafer.

5. The local purging tool of claim 1, wherein the aperture is located within the permeable portion of the surface of the purging chamber.

6. The local purging tool of claim 1, wherein the permeable portion of the surface of the purging chamber comprises:
    a first portion comprising a permeable media; and
    a second portion comprising a differential grade permeable media,
    wherein the second portion comprises higher grade permeable media than the first portion.

7. The local purging tool of claim 6, wherein the aperture is located within the second portion of the permeable portion of the surface of the purging chamber.

* * * * *